United States Patent [19]

List

[11] Patent Number: 5,807,571
[45] Date of Patent: Sep. 15, 1998

[54] TRANSDERMAL THERAPEUTIC SYSTEMS FOR ADMINISTERING INDOLE SEROTONIN AGONISTS

[75] Inventor: Harald List, Neuwied, Germany

[73] Assignee: LTS Lohmann Therapie-Systeme GmbH, Neuwied, Germany

[21] Appl. No.: 946,658

[22] Filed: Oct. 7, 1997

Related U.S. Application Data

[63] Continuation-in-part of Ser. No. 545,702, Nov. 6, 1995, abandoned.

[30] Foreign Application Priority Data

May 6, 1993 [DE] Germany ............... 43 14 976.6

[51] Int. Cl.$^6$ ...................................... A61F 13/00
[52] U.S. Cl. ..................... 424/449; 424/447; 424/448; 424/489
[58] Field of Search ................... 424/447, 448, 424/449, 489

[56] References Cited

U.S. PATENT DOCUMENTS

| | | | |
|---|---|---|---|
| 3,742,951 | 7/1973 | Zaffaroni | 424/449 |
| 3,797,494 | 3/1974 | Zaffaroni | 424/449 |
| 3,996,934 | 12/1976 | Zaffaroni | 424/449 |
| 5,079,008 | 1/1992 | Sinnreich et al. | 424/448 |

FOREIGN PATENT DOCUMENTS

| | | |
|---|---|---|
| 0 500 086 | 8/1992 | European Pat. Off. |
| 3 527 648 | 2/1986 | Germany |

*Primary Examiner*—D. Gabrielle Brouillette
*Attorney, Agent, or Firm*—Wenderoth, Lind & Ponack, L.L.P.

[57] ABSTRACT

The invention relates to transdermal therapeutic system for the systemic administration of active substances which is characterized by the fact that at least one of the active substances is a serotonin agonist of the group comprising the indole derivatives, e.g., Sumatriptan.

18 Claims, No Drawings

TRANSDERMAL THERAPEUTIC SYSTEMS FOR ADMINISTERING INDOLE SEROTONIN AGONISTS

This application is a continuation-in-part of U.S. application Ser. No. 08/545,702 filed Nov. 6, 1995, now abandoned (which is a 371 of PCT/EP 94/01280, filed Apr. 25, 1994).

The present invention relates to transdermal therapeutic systems for the systemic administration of active substances, to a process for the production thereof and to the use of these systems for the treatment of diseases.

Many people suffer from migrainous headache whose pathophysiology has not been elucidated so far: both a severe dilatation of the cerebral blood vessels and a perivascular aseptic inflammation in the region of the dural arteries are regarded as the causes. The neurotransmitter serotonin (5-hydroxytryptamine, 5-HT) is said to play a key role in regulating the vascular tone.

Frequently, migraine is accompanied by sickness and vomiting and a sensitivity to light and noise. Cluster headache is a very intense hemicrania occurring in intervals.

These complaints are treated by administering pain relieving drugs (analgesics, such as ASS (acetylsalicylic acid), or paracetamol) and/or substances tonizising the vessels (dihydroergotamine), in case of sickness and vomiting, preferably in the form of injections or rectal applications but also as controlled dosage aerosols. However, in many cases the effect of such therapeutic procedures is insufficient—for example, the vasoconstrictive action of ergotamine is not selectively limited to the cerebral vessels and results in undesired side effects.

To reduce the frequency of migraine attacks, betablockers, calcium antagonists and $5\text{-}HT_2$-antagonists are prophylactically employed with varying success.

The use of serotonin itself which seems to be obvious at first, is not appropriate from the therapeutic point of view, since 5-HT acts on various organ systems and many undesired concomitant effects occur. Serotonin was given its name because of the powerful vasoconstrictive action.

Serotonin deficiency results in a vasodilatation causing the migrainous headache. The onset of action is effected via $5\text{-}HT_1$-receptors in the region of the vascular walls of cerebral arteries.

In the last few years, the chemical structure of serotonin has been modified in various manners, resulting in changes of the pharmacological properties. For example, indole derivatives were synthesized which cause the cerebral vessels to be selectively tonizised (contracted) combined with a rapid improvement of the symptoms. These are so-called serotonin agonists having a particular affinity for $5\text{-}HT_1$-receptors.

The indole derivatives which can be used as serotonin agonists in transdermal therapeutic systems for the treatment of migraine and cluster headache have the following general formula I:

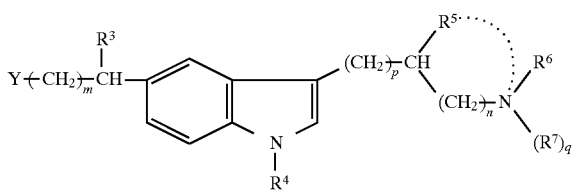

wherein:

Y represents a group of the formulae

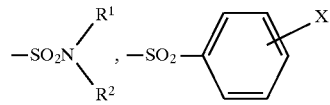

or a 5- or 6-membered cycloalkyl, wherein 1, 2 or 3 $CH_2$-groups may be replaced by O, S or NH, and which cycloalkyl may be substituted with an oxo group, X represents hydrogen, $C_{1-3}$-alkyl, $C_{1-3}$-alkoxy, halogen, $CF_3$, $NO_2$ or $NH_2$;

$R^1$ represents hydrogen, $C_{1-6}$-alkyl or $C_{3-6}$-alkenyl;

$R^2$ represents hydrogen, $C_{1-3}$-alkyl, $C_{3-6}$-alkenyl, aryl, aryl($C_{1-4}$)alkylene or $C_{5-7}$-cycloalkyl;

$R^3$ represents hydrogen or $C_{1-3}$-alkyl;

$R^4$ represents hydrogen, $C_{1-6}$-alkyl or $C_{3-6}$-alkenyl;

$R^5$ represents hydrogen or the group $(CH_2)_r$;

$R^6$ and $R^7$ which may be the same or different, each represent a hydrogen atom or $C_{1-3}$-alkyl;

m, n and r, which may be the same or different, represent an integer of 0 to 3;

p represents an integer of 0 or 1;

q represents an integer of 0 or 1;

with the proviso, that when $R^5$ represents the group $(CH_2)_r$ and r is not zero, this group can be bound to the nitrogen atom of the radical $NR^6(R^7)_q$ by a single bond, in which case q is zero, or a physiologically acceptable salt or solvate thereof.

The term "aryl" as aforementioned shall mean a 6 to 10 membered aromatic ringsystem, which may be substituted 1 to 3-times with $C_{1-3}$-alkyl, $C_{1-3}$-alkoxy, halogen, $CF_3$, $NO_2$ or $NH_2$.

The preferred meaning is phenyl, which is unsubsituted or substituted one time with one of the above mentioned radicals.

Preferred for the above-mentioned use are those compounds of the formula I, wherein $R^3$ is hydrogen, $R^4$ is hydrogen and m is 0 or 1.

Particularly preferred are compounds of the formula I, wherein $R^3$, $R^4$ and m are as defined above, and Y is a group of the formula $-SO_2NR^1R^2$, where $R^1$ is hydrogen and $R^2$ is $C_{1-3}$-alkyl, or Y is a group of the formula

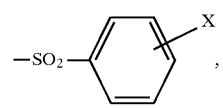

where X is hydrogen, or Y is a 5- or 6-membered cycloalkyl, wherein one $CH_2$-group is replaced by an oxygen atom and another $CH_2$-group by the group NH.

Also particularly preferred compounds are those of the formula I wherein $R^3$, $R^4$ and m are as defined above and $R^5$ is hydrogen, $R^6$ and $R^7$ are the same and represent $C_{1-3}$-alkyl, p is 0, n is 0 or 1 and q is 1.

Further particularly preferred compounds are those of the formula I, where $R^3$, $R^4$ and m are as defined above, $R^5$ is the group $(CH_2)_r$, which is bound to the nitrogen atom of the radical $NR^6(R^7)q$ by a single bond, $R^6$ represents $C_{1-3}$-alkyl, p is 0 or 1, q is 0, n and r are either both 2, or n is 0 and r is 3.

The most preferred indole serotonin agonists for the above-mentioned use are the following compounds of formula I:

3-[2-(dimethylamino)ethyl]-N-methyl-1H-indole-5-methanesulfonamide (INN: SUMATRIPTAN)
3-(1-methyl-4-piperidinyl)-N-methyl-1H-indole-5-ethanesulfonamide (INN: NARATRIPTAN)
(R)-3-[(1-methyl-2-pyrrolidinyl)methyl]-1H-indole-5-[2-(phenylsufonyl)ethyl] (INN: ELETRIPTAN)
(S)-4-[[3-[2-dimethylaminoethyl]-1H-indol-5-yl]methyl]-2-oxazolidinone (INN: ZOLMITRIPTAN)

The synthesis of the compounds of the formula I can be carried out according to the following references: British Patents No. 2 124 210 B and 2 162 522 B and EP-0 500 086 A (SUMATRIPTAN and derivatives).
EP-A-303 507; U.S. Pat. No. 4,997,841 (NARATRIPTAN and derivatives)
EP-A-592 438; U.S. Pat. No. 5,545,644; WO 9206973 (ELETRIPTAN and derivatives)
EP-A-486 666; EP-A-636 623; U.S. Pat. No. 5,399,574; U.S. Pat. No. 5,466,699; WO 91/18897 (ZOLMITRIPTAN and derivatives).

In the meantime, the pharmacological findings with respect to SUMATRIPTAN and the other mentioned serotonic agonists are reflected in many patents describing oral, parenteral and intranasal as well as rectal applications (e.g., DE 35 27 648, EP 503 440 and EP 500 086). The use of the active substances in transdermal therapeutic systems is not mentioned therein.

The disadvantages of SUMATRIPTAN are due to the pharmacokinetics: the half-life of SUMATRIPTAN after subcutaneous and oral application merely amounts to about 2 hours. The bioavailability in case of oral application merely amounts to 14% due to the presystemic metabolism, while it amounts to 96% when injected subcutaneously. Owing to the short half-life of SUMATRIPTAN the migraine symptoms can soon occur again, requiring new application.

When injected, side effects may occur as a burning and redness at the puncture point, when administered orally, the bitter taste can be avoided by coating the tablet. Also, a temporary sensation of heat, pressure, narrowness or heaviness is generally observed after the application of SUMATRIPTAN. A constriction of systemic arteries is to be considered with patients suffering from hypertension or coronary heart diseases.

It is the object of the present invention to find an administration form avoiding the described disadvantages and increasing the efficacy of the active substance.

The above object is achieved by a transdermal therapeutic system according to claim 1, by a process for the production thereof according to claim 16 and methods of treatment according to claims 17 and 18. The sub claims relate to preferred embodiments of the present invention.

The invention relates to a transdermal therapeutic system for the systemic administration of active substances which is characterized by the fact that at least one of the active substances is an indole serotonin agonist according to formula I and/or its pharmaceutically acceptable salts.

In a particularly preferred embodiment SUMATRIPTAN (3-(2-(dimethylamino)-N-methyl-1H-indole-5-methanesulfonamid or one of its derivatives is used as active substance.

Additionally the present invention relates to a process for producing the transdermal therapeutic system for the systemic administration of active substances, wherein an effective amount of at least one active substance is introduced into the system in solid or microencapsulated form, in solution or in dispersion.

Accordingly, a transdermal therapeutic system is used which achieves a systemic effect due to transdermal absorption.

A therapeutic system is defined as a drug-containing device or administration form continuously releasing one or more drugs at a predetermined rate over a defined period of time to a defined site of application (quoted according to Heilmann "Therapeutische Systeme", Ferdinand-Enke-Verlag, Stuttgart 1984).

The advantages of a TTS lie in the continuous active substance release, improved pharmacodynamics of substances having a short half-life, increased efficiency by avoiding the first-pass effect of the liver, avoiding discomfort and risks of an intraveneous treatment, avoiding side effects in the region of the gastrointestinal tact in case of oral medication, and good patient acceptance. Absorption peaks involving the risk of systemic side effects are avoided. As compared to the repeated application required in some cases, the total dose can be reduced.

Sickness and vomiting typically occuring in migraine make an oral application of the active substance impossible so that—from this point of view too—the administration by means of a transdermal therapeutic system offers considerable advantages. In this respect a TTS may have different designs and structures, corresponding to the latest state of the art.

The technical realization of transdermal therapeutic systems is possible on the basis of the following fundamental solutions which have resulted in respective products on the market:

1. membrane controlled systems
2. matrix controlled systems.

The object of the systems is to ensure a controlled, generally constant active substance release over a defined period of time.

Patches formed as membrane controlled system are disclosed, for example, in U.S. Pat. Nos. 3,742,951; 3,797,494; 3,996,934 and 3,031,894. In principle these patches consist of a backing layer representing one surface, a pressure sensitive adhesive layer permeable to the active substance and representing the other surface, and, finally, a reservoir comprising the active substance between the two layers forming the surfaces.

Alternatively, the active substance may be contained within a variety of microcapsules distributed within a pressure sensitive adhesive layer which is permeable to the active substance. In this case the material of the capsule may also act as controlling membrane.

A patch as matrix controlled system (i.e., with matrix-diffusion-control) is described in DE-PS 33 15 272, for example. It consists of an impermeable backing layer, a reservoir of a polymeric matrix, which is attached to the backing layer and has a particular construction and comprises the active substance at a concentration which optionally is above the saturation concentration, a pressure sensitive adhesive layer bonded to the reservoir and permeable to the active substance, and a protective layer which covers the pressure sensitive adhesive layer and can be removed prior to use may also be present. If the reservoir matrix itself is pressure sensitive adhesive, the additional pressure sensitive adhesive layer may be dispensed with.

According to a particular embodiment of the present invention, the TTS as matrix controlled system in the form of a patch comprises a backing layer, an active substance reservoir connected therewith and having a polymeric matrix controlling the release of active substances, and a pressure sensitive adhesive layer permeable to the active substances to attach the system to the skin.

In particular, a TTS whose active substance reservoir comprises the active substances at a concentration above the saturation concentration proves to be excellently suitable to solve the problem stated in the present invention.

In a particular embodiment of the invention the transdermal therapeutic system for the systemic administration of active substances may comprise as active substance SUMATRIPTAN (3-(2-(dimethylamino)ethyl)-N-methyl-1H-indole-5-methanesulfonamide) or one of its derivatives.

In further particular embodiments of the invention the above system may comprise as active substance the compounds NARATRIPTAN, ELETRIPTAN and ZOLMITRIPTAN.

Preferably, a TTS can be used which comprises a protective layer that can be removed from the pressure sensitive adhesive layer. The TTS in patch form according to the present invention proved to be particularly suitable when an impermeable backing layer was used.

The dosage of SUMATRIPTAN or another pharmacologically acceptable indole derivative must be selected such that the effective serum level is achieved during the intended period of application. For SUMATRIPTAN these serum levels amount to about 50 to 70 μg per liter.

These TTS are used for the production of a ready-for-use drug. For this purpose parameters have to be defined, e.g., choice of active substance, dosage, control of release and release rate, composition of the reservoir, and addition of adjuvants.

It may be useful to add as adjuvants at least one representative of the group comprising penetration enhancers, anti-ageing agents, stabilizers, carriers, blood flow stimulants, and fillers. Suitable penetration enhancers include, for example, carboxylic acids, such as octanoic acid, stearic acid, oleic acid, etc. The use of the abovementioned additives which—among others—depends on the kind of the active substances, are known to those skilled in the art.

Also, another principle of improving the permeation of active substances through the skin can be considered, i.e., the application of electric current (iontophoresis). The active substances may be introduced into a TTS in different forms (solid, in solution, in dispersion); they may also be microencapsulated. The content of SUMATRIPTAN, NARATRIPTAN, ELETRIPTAN and ZOLMITRIPTAN, respectively, of such an administration system preferably amounts to between 10 and 200 mg.

In this connections it becomes apparent that the TTS for the systemic administration of active substances according to the present invention is particularly suitable for the production of a drug for the treatment of migraine and cluster headache.

Finally, it may be useful to combine serotonin agonists with another active substance—aiming at a potentiation of action, sometimes, however, at a reduction of the single doses (e.g., with analgesics, antimimetics, psychopharmacologic agents, or sedatives).

I claim:

1. A transdermal therapeutic system for the systemic administration of active substance having at least one indole serotonin agonist as the active substance, said transdermal system being in the form of a patch comprising
   (i) a backing layer,
   (ii) an active substance reservoir connected thereto,
   (iii) in the absence of other controlling mechanisms a membrane which controls the release of said serotonin agonist, and
   (iv) a pressure sensitive adhesive portion for fixing the system to the skin the active substance reservoir containing said agonist in a concentration which is above the saturation concentration, and the system containing at least one adjuvant selected from the group consisting of penetration enhancers, anti-ageing agents, stabilizers, carriers, blood flow stimulants and fillers.

2. A transdermal therapeutic system according to claim 1 wherein the indole serotonin agonist is a compound of the general formula I

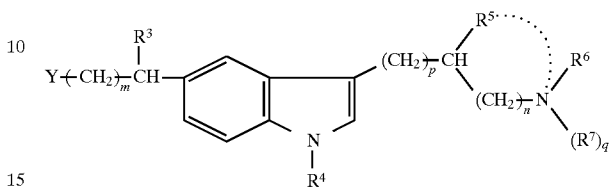

wherein:

Y represents a group of the formulae

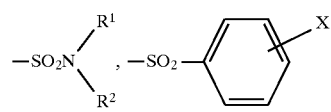

or a 5- or 6-membered cycloalkyl, wherein 1, 2 or 3 $CH_2$-groups may be replaced by O, S or NH, and which cycloalkyl may be substituted with an oxo group;

X respresents hydrogen, $C_{1-3}$-alkyl, $C_{1-3}$-alkoxy, halogen, $CF_3$, $NO_2$ or $NH_2$;

$R^1$ represents hydrogen, $C_{1-6}$-alkyl or $C_{3-6}$-alkenyl;

$R^2$ respresents hydrogen, $C_{1-3}$-alkyl, $C_{3-6}$-alkenyl, aryl, aryl($C_{1-4}$)alkylene or $C_{5-7}$-cycloalkyl;

$R^3$ represents hydrogen or $C_{1-3}$-alkyl;

$R^4$ represents hydrogen, $C_{1-6}$-alkyl or $C_{3-6}$-alkenyl;

$R^5$ represents hydrogen or the group $(CH_2)_r$;

$R^6$ and $R^7$ which may be the same or different, each represent a hydrogen atom or $C_{1-3}$-alkyl;

m, n and r, which may be the same or different, represent an integer of 0 to 3;

p represents an integer of 0 or 1;

q represents an integer of 0 or 1;

with the proviso that when $R^5$ represents the group $(CH_2)_r$, and r is not zero, this group can be bound to the nitrogen atom of the radical $NR^6(R^7)q$ by a single bond, in which case q is zero, or a physiologically acceptable salt or solvent thereof.

3. A transdermal therapeutic system according to claim 2, wherein the indole serotonin agonist is a compound of the general formula I, where $R^3$ is hydrogen, $R^4$ is hydrogen and m is 0 or 1.

4. A transdermal therapeutic system according to claim 3, wherein the indole serotonin agonist is a compound of the general formula I, where Y is a group of the formula $—SO_2NR^1R^2$, where $R^1$ is hydrogen and $R^2$ is $C_{1-3}$-alkyl, or of the formula

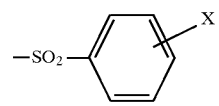

where X is hydrogen, or Y is a 5- or 6-membered cycloalkyl, wherein one $CH_2$-group is replaced by oxygen and another $CH_2$-group by —NH.

5. A transdermal therapeutic system according to claim 3, wherein the indole serotonin agonist is a compound of the general formula I, where $R^5$ is hydrogen, $R^6$ and $R^7$ are the same and represent $C_{1-3}$-alkyl, p is 0, n is 0 or 1 and q is 1.

6. A transdermal therapeutic system according to claim 3, wherein the indole serotonin agonist is a compound of the general formula I, where $R^5$ is the group $(CH_2)_r$, which is bound to the nitrogen of the radical $NR^6(R^7)_q$ by a single bond, $R^6$ represents $C_{1-3}$-alkyl, p is 0 or 1, n and r are either both 2, or n is 0 and r is 3.

7. A transdermal therapeutic system according to claim 3, wherein the indole serotonin agonist is 3-[2-(dimethylamino)ethyl]-N-methyl-1H-indole-5-methanesulfonamide (SUMATRIPTAN) or a physiologically acceptable salt or solvate thereof.

8. A transdermal therapeutic system according to claim 3, wherein the indole serotonin agonist is 3-(1-methyl-4-piperdinyl)-N-methyl-1H-indole-5-ethansulfonamide (NARATRIPTAN) or a physiologically acceptable salt or solvate thereof.

9. A transdermal therapeutic system according to claim 3, wherein the indole serotonin agonist is (R)-3-[(1-methyl-2-pyrrolidinyl)methyl]1H-indole-5-[2-(phenylsulfonyl)ethyl] (ELETRIPTAN) or a physiologically acceptable salt or solvate thereof.

10. A transdermal therapeutic system according to claim 3, wherein the indole serotonin agonist is (S)-4-[[3-[2-dimethylaminoethyl]-1H-indole-5-yl]methyl]-2-oxazolidinone ZOLMITRIPTAN) or a physiologically acceptable salt or solvate thereof.

11. A trandermal therapeutic system according to claim 1 wherein at least one serotonin agonist is present in a microencapsulated form.

12. A transdermal therapeutic system according to claim 1, wherein the wall of the material of the capsule is formed as a membrane.

13. A transdermal therapeutic system according to claim 1, wherein the system has a protective layer which can be removed from the pressure sensitive adhesive layer.

14. A transdermal therapeutic system according to claim 1, wherein the backing layer is impermeable to the components of the reservoir.

15. A transdermal therapeutic system according to claim 1, which comprises 10 to 200 mg of an indole serotonin agonist selected of the group consisting of SUMATRIPTAN, NARATRIPTAN, ELETRIPTAN and ZOLMITRIPTAN.

16. A process for the production of the transdermal therapeutic system for the systemic administration of active substances according to claim 1, which comprises including an effective amount of an indole serotonin agonist into the system in solid form, in microencapsulated form, in solution or in dispersion.

17. A method for treating a person suffering from migraine or cluster headache which comprises administering to said person a transdermal therapeutic system as defined in claim 1.

18. A method according to claim 17 wherein the administration is accompanied by the application of electrical current as penetration enhancer.

* * * * *